United States Patent [19]

Caldwell et al.

[11] 4,118,469

[45] Oct. 3, 1978

[54] ANTIGEN FOR TRACHOMA LYMPHOGRANULOMA VENEREUM (LGV) AND NON-GONOCOCCAL URETHRITIS (NGU)

[75] Inventors: Harlan D. Caldwell; Cho-Chou Kuo; George E. Kenny, all of Seattle, Wash.

[73] Assignee: Research Corporation, New York, N.Y.

[21] Appl. No.: 680,927

[22] Filed: Apr. 27, 1976

[51] Int. Cl.² .................... G01N 33/16; A61K 43/00
[52] U.S. Cl. ................................ 424/1; 23/230 B; 260/112 R; 424/12
[58] Field of Search .............. 424/1, 12; 23/230 B; 260/112 R

[56] References Cited

U.S. PATENT DOCUMENTS

| 2,355,676 | 8/1944 | Rake et al. | 424/12 |
| 2,415,234 | 2/1947 | Bunney et al. | 424/12 |
| 3,646,346 | 2/1972 | Catt | 424/1 X |

OTHER PUBLICATIONS

Collins et al., Chemical Abstracts, vol. 72, No. 11, Mar. 16, 1970, p. 216, abstract No. 53182d.
Haider et al., Chemical Abstracts, vol. 74, No. 3, Jan. 18, 1971, p. 175, abstract No. 11472j.
Chemical Trade Names and Commercial Synonyms, Haynes, Van Nostrand Co., Inc., NY, 1955, p. 428.

*Primary Examiner*—Benjamin R. Padgett
*Assistant Examiner*—Christine M. Nucker
*Attorney, Agent, or Firm*—Cooper, Dunham, Clark, Griffin & Moran

[57] ABSTRACT

Solubilized antigens of *C. trachomatis* strain LGV-434 upon analysis using two-dimensional immunoelectrophoresis yielded a single antigen which was found to be consistently precipitated by sera of patients with *C. trachomatis* infections. This antigen as antigen-antibody complex was employed as an immunogen to prepare a rabbit monospecific antiserum to this component or antigen. This monospecific antiserum demonstrated the presence of the antigen in each of the 15 strains of *C. trachomatis* organisms and was non-reactive with strains of *C. psittaci*. The *C. trachomatis* specific antigen was purified by immunoadsorption chromatography using monospecific antiserum as a specific ligand covalently bound to agarose gel columns and the resulting purified antigen employed to detect antibody from the sera of lymphogranuloma venereum patients using counterimmunoelectrophoresis. When the *C. trachomatis* specific antigen is isotopically labeled and utilized in the highly sensitive radioimmune assay antibody to the antigen should be demonstrated and a serological test based thereon should be applicable for the serological diagnosis of non-gonococcal urethritis (NGU).

18 Claims, No Drawings

ANTIGEN FOR TRACHOMA LYMPHOGRANULOMA VENEREUM (LGV) AND NON-GONOCOCCAL URETHRITIS (NGU)

This invention was made with the financial support of the Department of Health, Education and Welfare.

*Chlamydia trachomatis* organisms are the etiological agents for a number of human ocular-genital diseases, such as ocular trachoma, lymphogranuloma venereum (LGV) and non-gonococcal urethritis (NGU). The most important of these diseases in the United States is NGU. The annual incidence of NGU exceeds that of gonorrhea and it is estimated that there occur more than 2,000,000 cases of NGU yearly in the United States alone.

There are 15 different immunotypes of *C. trachomatis*, 12 of which have been associated with NGU. At present, the only serological test used in the diagnosis of NGU is the microimmunofluoresence test. This test is only available in a limited number of research laboratories throughout the world. This test requires that all 15 strains of *C. trachomatis* organisms be used as serological test antigen. Accordingly, this test is very laborious, time-consuming, expensive and difficult to perform. There is no commercially available antigen that can be used for serological testing. Ideally, a serological test antigen for NGU, as well as for LGV, would be one that is shared by each of the *C. trachomatis* strains to which infected individuals make antibody to during the course of infection.

Accordingly, it is an object of this invention to prepare an antigen of *C. trachomatis* useful in the serological testing for LGV and/or NGU.

It is another object of this invention to provide a technique and compositions employing the aforesaid antigen for the serological diagnosis of LGV and/or NGU.

How these and other objects of this invention are achieved will become apparent in the light of the accompanying disclosure. In at least one embodiment of the practice of this invention at least one of the foregoing objects will be achieved.

An antigen which is common to all strains of *C. trachomatis* organisms has been identified. Patients with *C. trachomatis* infections were found to consistently recognize this antigen and the antigen, when purified, was used to detect specific antibody in sera from lymphogranuloma venereum patients using counterimmunoelectrophoresis. It is mentioned that ideally a serological test antigen for NGU would be one that is shared by each of the *C. trachomatis* strains to which infected individuals make antibody during the course of infection. The antigen of this invention appears to meet this criterion. As mentioned hereinabove, the antigen was used to detect specific antibody in sera from lymphogranuloma venereum patients using counterimmunoelectrophoresis. This test procedure, counterimmunoelectrophoresis, employing the antigen is suitable for the testing of LGV since LGV patients commonly exhibit much higher levels of antibody than patients with NGU. When the antigen would be employed for the testing of NGU, a more sensitive serological test would be employed, such as radioimmunoassay, utilizing the isotopically labeled antigen. Accordingly, the isotopically labeled antigen of this invention when employed in the highly sensitive radioimmune assay would be useful for the detection of antibody from sera of NGU patients.

By way of a general description with respect to the production of the *C. trachomatis* specific protein antigen in accordance with this invention, solubilized antigens of *C. trachomatis* strain LGV-434 employing a non-ionic surfactant or detergent, such as Triton X-100 (an alkyl aryl polyether alcohol), as the solubilizing agent were obtained. The detergent-soluble antigens were than analyzed using two-dimensional immunoelectrophoresis. There was obtained from these antigens a single antigen which was found to be consistently precipitated by the sera of patients with *C. trachomatis* infections. Specifically, employing two-dimensional immunoelectrophoresis, this specific antigen was excised from agarose gels as antigen-antibody complex and this complex was used as an immunogen to prepare rabbit monospecific antiserum to this antigen or component. The resulting monospecific antiserum was used to demonstrate the presence of antigen on each of the 15 strains of *C. trachomatis* organisms. It was observed that this monospecific antiserum was not reactive with strains of *C. psittaci*, thereby demonstrating the antigen's species specificity.

This *C. trachomatis* specific antigen was purified by immunoadsorption chromatography using the monospecific antiserum as a specific ligand covalently bound in an agarose gel column. The resulting purified antigen was used successfully to detect antibody from the sera of LGV patients using counterimmunoelectrophoresis and 96% of the cases tested were found to be positive. Although this type of test, counterimmunoelectrophoresis, is not useful for the detection of antibody from the sera of NGU patients, because of the low concentration of antibody therein, antibody to the antigen could be detected using two-dimensional immunoelectrophoresis. The differences in the results obtained reflect the relative differences of these two serological tests for the detection of antibody. Accordingly, if the *C. trachomatis* specific antigen herein were isotopically labeled and utilized in the highly sensitive radioimmune assay antibody to the antigen in the sera of NGU patients, this technique would be more useful and, accordingly, a serological test based on radioimmune assay employing the isotopically labeled specific antigen herein would be readily applicable for the serological diagnosis of NGU.

Our publications entitled ANTIGENIC ANALYSIS OF CHLAMYDIAE BY TWO-DIMENSIONAL IMMUNOELECTROPHORESIS I. Antigenic Heterogeneity betwen C. trachomatis and C. psittaci and II. A Trachoma-LGV-Specific Antigen, which appeared in *The Journal of Immunology*, Vol. 115, No. 4, pages 963–968 and 969–975, October 1975, describe the preparation of the specific antigen of this invention, the trachoma-LGV-specific antigen, and the utility of this antigen in serodiagnosis, particularly for LGV. The disclosures of each of the above-identified publications are herein incorporated and made part of this disclosure.

As described in the above-identified publication II. — A Trachoma-LGV-Specific Antigen, certain antigens of Chlamydia were solubilized with a non-ionic detergent, specifically Triton X-100, and these solubilized antigens or strains of *C. trachomatis* and *C. psittaci* were found to be strikingly heterogeneous when analyzed by immunoelectrophoresis, see publication I. Antigen Heterogeneity between *C. trachomatis* and *C. psittaci*. However, because of the promising species-specificity of the solubilized antigens, the human sera of patients with diagnosed *C. trachomatis* infections were tested. It was found that one of the solubilized antigens of lymphogranuloma venereum strain LGV-434 was strongly and consistently precipitated by the patient's sera. This particular antigen, the antigen of this invention, was further studied and there is presented hereinafter the results of the studies of this specific antigen. These results indicate that this antigen is *C. trachomatis* species-specific and indicate its utility as a specific test antigen in the serodiagnosis of trachoma and LGV infections.

In the tests demonstrating this invention the *C. trachomatis* strains used were A/G-17/OT, B/TW-5/OT, Ba/Ap-2/OT, C/TW-3/OT, D/UW-3/Cx, E/UW-41/Cx, F/UW-50/Cx, G/UW-57/Cx, H/UW-43/Cx, I/UW-97/Ur, K/UW-31/Cx, K/UW-53/Cx, $L_1$/440/Bu, $L_2$/434/Bu, $L_3$/404/Bu, and mouse pneumonitis (MoPn)/Nigg. *C. psittaci* strains used were meningopneumonitis (Mn)/Cal-10, feline pneumonitis (FP)/Baker and psittacosis/6BC, see Gordon, F. B. and Quan, A. L., J. Infect. Dis., 115: 186, 1965.

Serologic test antigens: Strains 434 and Mn were grown in suspension cultures of mouse L-929 cells with the medium supplemented with 10% horse serum and the organisms were purified by pelleting through 30% renografin (methylglucamine diatrizoate, 76% for injection. The partially purified organisms were resuspended in 0.01 M phosphate-buffered saline (PBS) containing 1% (v/v) Triton X-100 (Calbiochem, San Diego, Calif.), pH 7.2. Insoluble material was removed by centrifugation at 30,000 × G for 30 minutes. The supernatant was then concentrated with centriflo membrane cones CF-50 (Amincon Corp., Lexington, Mass.) to contain 10 mg protein/ml and used as test antigen.

Antigens of TW-5, UW-31, and MoPn were grown in human heteroploid (HeLa 229) cells in monolayer culture with the medium supplemented with 10% fetal calf serum. The organisms were purified by one cycle of differential centrifugation (500 × G for 15 minutes and 30,000 × G for 30 minutes), pelleted through 30% renografin, solubilized in 1% Triton X-100 and standardized to contain 10 mg protein/ml. The solubilized antigens from organisms grown in HeLa 229 cells were reacted only with rabbit anti-antigen-0.65 monospecific antiserum.

Immunogens: Strains 434, UW-31 and Mn were grown in HeLa 229 cells and the organisms were purified as described above. Concentrated organisms were resuspended in PBS and standardized to contain 7 to 8 × $10^{10}$ organisms/ml by an electronmicroscopic method, see Wang, S. P. and Grayston, J. T., Am. J. Ophthalmol., 63: 1443, 1967.

Antisera production: New Zealand white rabbits were used to raise all antisera. Total immunizing dose was 2 to 3 × $10^{11}$ organisms per rabbit.

Monospecific antiserum: Monospecific antiserum was prepared in rabbits by using as immunogens, material obtained by excising precipitin lines from the two-dimensional electrophorograms as has been described by Crowle, A. J., Revis, G. J., and Jarrett, K., Immunol. Commun., 1: 325, 1972. One hundred micrograms of detergent-solubilized 434 antigen was electrophoresed and precipitated in the second phase of electrophoresis with a homologous antiserum (rabbit anti-434). The antiserum concentration in the second gel was reduced so that the precipitin line to be excised was distinct and clearly separated from other precipitates. Slides were washed in 10 mM TES saline [0.15 M NaCl in Tris (hydroxy-methyl) methyl-2-aminoethanesulphonic acid], pH 7.0 for 24 hours followed by a 24-hour wash in distilled water before the removal of precipitin lines. Agarose-containing antigen-antibody complexes were suspended in PBS and emulsified in an equal volume of Freund's complete adjuvant. Three-tenths milliliter of the suspension was injected intradermally into rabbits at three separate sites. Two injections were given in the inguinal region (one injection per side) and a single injection in the nuchal region of the neck. After 14 days rabbits were injected intramuscularly (i.m.) with 1 ml of aqueous antigen without adjuvant. Rabbits were bled 10 days after the i.m. injection and then immunized i.m. with 1 ml of aqueous antigen at 6- to 8-week intervals. Bleedings were done 10 days after each i.m. immunization. Each immunization consisted of pooled precipitates from 12 two-dimensional electrophoresis slides.

Human sera: Sera used in two-dimensional immunoelectrophoresis were obtained from diagnosed cases of *C. trachomatis* infections of LGV, ocular trachoma (OT), non-gonococcal urethritis (NGU) and cervicitis (NGC), cases of psittacosis, and chancroid and normal persons. Ten normal sera from individuals without disease or demonstrable antibody to Trachoma-LGV by micro-IF were used as negative controls.

Two-dimensional electrophoresis: Glass-mounting slides (4 × 4 cm) were covered with 3 ml of 0.5% agarose in pH 8.6 barbital buffer, ionic strength 0.05, with 0.5% Triton X-100 and 0.01% sodium azide. Five microliters (50 μg protein) of solubilized antigen was electrophoresed in the first dimension at 2.7 volts/cm (5 mA/slide) for 1 hour and 50 minutes. The second dimension gel was 1.8 ml of agarose containing 0.2 to 0.4 ml of antiserum. Second dimension electrophoresis was carried out at 2.7 volts/cm for 6 hours. After the electrophoresis, slides were submerged for 24 hour each in 10 mM TES saline and distilled water, air dried, and stained with Coomasie Brilliant Blue.

Peak suppression: Suppression of precipitin peak height (peak suppression) was done by adding an additional antiserum to the second phase of electrophoresis. Antibodies with specificities to a common or shared antigenic determinant could be identified in this manner. The presence of antibodies to the same antigen resulted in a decrease in the heights of precipitin lines when compared to the profile produced when a single antiserum was used in the second phase of the test.

Peak enhancement: The two-dimensional immunoelectrophoretic profile obtained with a mixture of equal quantities (50 μg protein) of two antigens was compared with that obtained with one of the antigens alone using the same antiserum for both tests. An increase of the precipitin peak height (peak enhancement) was observed if common components were present in the two antigen preparations.

Determination of electrophoretic mobility of antigens: Five microliters (1 mg/ml) of bovine serum albumin were added to the test antigen and 0.05 ml of rabbit antibovine serum albumin was incorporated in the second-dimension gel when performing two-dimensional electrophoresis. The volume of rabbit anti-bovine serum albumin incorporated in the second-dimensional gel was adjusted so that the precipitate formed would run off the slide in the form of a pillar. Electrophoretic migration distances were determined by drawing a line originating at the center of the antigen well and extending through the middle of the first phase run. A line perpendicular to the base was drawn which bisected the peaks. The electrophoretic mobility of an antigen was calculated relative to that of bovine albumin which was assigned a value of 1.0. The measurements were done with a slide viewer which provided a 5.5 × magnification.

Agar gel double immunodiffusion: 0.7 ml of 0.5% agarose in 10 mM TES saline, pH 7.0, was placed on a 4.5-cm space marked on a glass microscope slide. Plastic templates were placed on the agar surface. Reactants, antigen, and antibody were than added to the templates and the slides were incubated in a moist chamber for 48 hours at room temperature. The slides were washed for 24 hours each in 10 mM TES saline and distilled water, air dried, and stained with 0.5% Coomassie Brilliant Blue.

Indirect immunofluorescence staining of inclusions in HeLa cells: HeLa 229 cells, grown on a 12-mm round coverslip in a 1-dram (4 ml) flat bottomed vial, were infected with chlamydial strains. After 2 days of incubation, infected cells were fixed with methanol and air dried. Monospecific serum was applied on the cells and incubated at 37° C. for 30 minutes in a moist chamber. The cells were washed with PBS and applied with fluorescein isothiocyanate conjugated antirabbit γ-globulin goat serum and incubated at 37° C. for 30 minutes in a moist chamber. Finally, the cells were washed with PBS, air dried, mounted on a microscope slide, and observed for inclusions under a fluorescence microscope.

Preliminary study of rabbit antisera and human sera by two-dimensional electrophoresis: 434 antigen was tested against rabbit antisera made against other *C. trachomatis* strains and human sera from patients with diagnosed *C. trachomatis* infections. One antigenic component of 434 was found to be intensively and consistently recognized by these sera. This component was first identified by determining its electrophoretic mobility relative to bovine serum albumin. At least 19 precipitin lines were recognized on the original electrophorograms and the antigen described above was intensely precipitated. Since this antigen had an electrophoretic mobility of 0.65 relative to bovine albumin, the antigen is described as antigen-0.65.

Determination of the monospecificity of antiserum made against antigen-0.65: Rabbits were immunized with precipitin lines of precipitated antigen-0.65 excised from the agar gels. The antiserum obtained was shown to be monospecific for antigen-0.65 since the antiserum formed a single precipitin line with an electrophoretic mobility of 0.65 when reacted against solubilized 434 antigen. An additional test for the monospecificity of the antiserum was done using peak suppression. The addition of monospecific antiserum to the second phase of electrophoresis resulted only in the reduction of the peak height of antigen-0.65 of the prototype 434 profile. The volume of anti-434 serum used in the second phase of the tests was reduced so that the suppression of peak 0.65 could be easily visualized.

Demonstration of Trachoma-LGV specificity of antigen-0.65: The monospecific serum was specific for Trachoma-LGV organisms. When solubilized antigen of *C. trachomatis* strains TW-5, UW-31 and MoPn and the *C. psittaci* strain Mn were reacted against the monospecific serum by two-dimensional electrophoresis, a single precipitin line with an electrophoretic mobility of 0.65 was obtained with antigens of TW-5 and UW-31. No precipitin line was observed when antigens of MoPn and Mn were reacted with the antiserum. The antigenic identity of antigen-0.65 among strains 434, TW-5, and UW-31 were shown by peak enhancement. The addition of heterologous antigen to the first dimension of electrophoretic separation of antigens results in an increase of the peak height formed by common antigenic components provided that the components have similar electrophoretic mobilities. The peak height of antigen-0.65 of 434 organisms was shown to be clearly enhanced by the addition of homologous 434, TW-5, or UW-31 antigens, indicating that antigen-0.65 is a common antigen shared by strains 434, TW-5, and UW-31. But, peak enhancement was not observed when antigens of MoPn and Mn were mixed with 434 antigen and electrophoresed against the monospecific serum. When solubilized 434, TW-5, and UW-31 were reacted against the monospecific antiserum by double immunodiffusion, a single line with a reaction of identity was observed.

Demonstration of Trachoma-LGV specificity of antigen-0.65 by indirect immunofluorescence staining of inclusions in HeLa cells: Because of the difficulty and expense in preparing chlamydial serologic test antigen, it was not possible to demonstrate that antigen-0.65 was shared by each of the 14 immunotypes of Trachoma and LGV with two-dimensional electrophoresis or double immunodiffusion. It was possible, however, to show that antigen-0.65 was shared by each immunotype of Trachoma and LGV by indirect fluorescence antibody staining of chlamydial infected HeLa 229 cells with monospecific antiserum to antigen-0.65.

Table I shows that inclusions from each of the Trachoma and LGV immunotypes demonstrated fluorescence. Fluorescence was not observed for inclusions of cells infected with Mn, FP, 6BC, or MoPn. Strains which showed negative fluorescence were stained again at 1:5 dilution of the serum. Weak fluorescence was observed with MoPn inclusions. Inclusions of *C. psittaci* strains Mn, FP, and 6BC remained negative. Preimmune serum from rabbits immunized with precipitates of antigen-0.65 was used as a control and was found to be negative.

TABLE I

INDIRECT IMMUNOFLUORESENCE STAINING OF CHLAMYDIAL INCLUSIONS IN HeLa 229 CELLS WITH ANTI-ANTIGEN-0.65 MONOSPECIFIC RABBIT SERUM

| Immunotype/Strains/ | Staining of Inclusions | |
|---|---|---|
| Site of Isolation | Giemsa | Indirect FA* |
| *C. trachomatis* | | |
| A/G-17/OT | + | + |
| B/TW-5/OT | + | + |
| Ba/Ap-2/OT | + | + |
| C/TW-3/OT | + | + |
| D/UW-3/Cx | ++ | |
| E/UW-41/Cx | + | + |
| F/UW-50/Cx | + | + |
| G/UW-57/Cx | + | + |
| H/UW-43/Cx | + | + |
| I/UW-97/Ur | + | + |
| K/UW-53/Cx | + | + |
| L₁/440/Bu | + | + |
| L₂/434/Bu | + | + |
| L₃/404/Bu | + | + |
| Mouse pneumonitis | + | — |
| *C. psittaci* | | |
| Meningopneumonitis | + | — |
| Feline pneumonitis | + | — |
| 6BC | + | — |

*Stained with a 1:20 dilution of anti-antigen-0.65 rabbit serum. Endpoint titer: 1:320.

Identification of precipitins to antigen-0.65 in sera from patients with *C. trachomatis* infections: *The presence of precipitins with a specificity for antigen-0.65 in sera from patients with C. trachomatis infections was de-* tected using the peak suppression test. Five microliters (50 μg protein) of solubilized 434 antigen were electrophoresed against 0.2 ml of sera from diagnosed LGV, ocular trachoma, and NGU or NGC patients in the second phase of electrophoresis. In the peak suppression test, 0.2 ml of the monospecific serum was mixed with 0.2 ml of human serum in the second phase of electrophoresis. The electrophoresis profiles before and after the suppression were than compared. Sera from LGV patients consistently precipitated this antigen very intensely even though the number of components recognized by such sera varied greatly. In contrast, precipitins to antigen-0.65 from patients with diagnosed OT, NGU, or NGC were consistently much weaker. Fifteen of the 18 sera with demonstrable antibody to *C. trachomatis* as determined by micro-IF had precipitins to antigen-0.65, see Table II. Some sera were capable of precipitating as many as 17 distinct components, whereas others precipitated as few as three. The three negative sera demonstrated no other precipitins to solubilized 434 antigens and also had a low serum antibody titer to *C. trachomatis* organisms by micro-IF. Psittacosis sera from patients Ry and $V_2$-1220 with complement-fixation titers of 1:512 and 1:256, respectively, and without detectable antibody to *C. trachomatis* by micro-IF did not have precipitins to antigen-0.65. Patients' sera with venereal disease other than chlamydial etiology (chancroid) or from normal persons were negative both by micro-IF and two-dimensional immunoelectrophoresis. The number of precipitates recognized by patients' sera does not directly correlate with the micro-IF antibody titer. However, when any precipitates are recognized from the sera of patients with *C. trachomatis* infections, precipitins to antigen-0.65 were consistently present.

fetal calf serum, horse serum, and cell culture control, all at 10 mg/ml. Serum from rabbits immunized with Freund's complete adjuvant mixed with an equal volume of agarose gel suspended in PBS failed to react with solubilized 434 antigen by both two-dimensional electrophoresis and double immunodiffusion. Two-tenths milliliter of each human serum used in this study were reacted against 50 μg of L cell control antigen and were negative when analyzed by two-dimensional immunoelectrophoresis.

The classical approach to antigenic analysis of microorganisms is to fractionate the organism and purify given biochemical components frequently one at a time. These are then tested for serologic activity against hyperimmune serum and finally against human sera for serologic activity. The ultimate purposes of such an effort are to provide both efficient serologic test antigens and vaccines. An alternative approach is to use the whole organisms for serodiagnosis and vaccines. A number of examples with microorganisms can be found with both approaches. Diphtheria toxoid and tetanus toxoid are highly efficient purified immunogens. Whole virus vaccines have been used with considerable success, e.g., killed polio vaccine and influenza vaccine. Recently, considerable emphasis has been placed on the use of purified antigens for immunogens and serologic test antigens. For example, efforts have been made to utilize purified gonococcal pili for serologic testing and a purified meningococcal polysaccharide vaccine has been used with considerable success. In the case of chlamydial infections, research workers have been quite active in both immunoprophylaxis and serodiagnosis. Whole organisms have been used for vaccines although problems with hypersensitivity have diminished the effectiveness of this approach. For serodiagnosis, the

TABLE II

Detection of Precipitins to Antigen 0.65 by Two-Dimensional Immunoelectrophoresis in the Serum of Patients with *C. Trachomatis* Infections Using Peak Suppression with Anti-Antigen-0.65 Monospecific Rabbit Serum

| Patient No. | Clinical Diagnosis | *C. trachomatis* Infection* | | Serum Ab | Immuno-type | Two-Dimensional Immunoelectrophoresis | |
|---|---|---|---|---|---|---|---|
| | | Isolation | Site of Isolation | | | No. Precipitin Lines vs LGV-434 Ag | Precipitins to Antigen-0.65 |
| 440 | LGV | + | Bu | 4,096** | $L_1$ | 8 | + |
| AA-123 | LGV | + | Bu | 512 | $L_1$ | 17 | + |
| 514 | LGV | + | Bu | 1,024 | $L_2$ | 17 | + |
| 1575 | LGV | + | Bu | 1,024 | $L_2$ | 2 | + |
| AA-101 | LGV | + | Bu | 2,048 | $L_2$ | 3 | + |
| 470 | LGV | + | Bu | 128 | $L_2$ | 0 | |
| 404 | LGV | + | Bu | 256 | $L_3$ | 2 | + |
| AA-310 | LGV | — | Bu | 1,024 | $L_2$ | 3 | + |
| AA-307 | LGV | — | Bu | 4,096 | $L_2$ | 16 | + |
| AA-102 | LGV | + | Ur | 2,048 | $L_3$ | 17 | + |
| U-216 | NGU | + | Ur | 64 | J | 2 | + |
| CS-072 | NGC | + | Cx | 512 | K | 2 | + |
| CS-014 | NGC | + | Cx | 128 | B | 0 | |
| VM-249 | NGU | + | Ur | 128 | H | 0 | |
| LB-9 | Trachoma | + | Ey | 512 | B | 3 | + |
| LB-2 | Trachoma | + | Ey | 128 | C | 2 | + |
| YB-13 | Trachoma | + | Ey | 256 | C | 3 | + |
| CS-151 | Normal | + | Cx | 2,048 | F | 7 | + |
| U-115 | NGU | + | Ur | 0 | D | 0 | |
| AA-305 | LGV | — | Bu | 0 | | 0 | |
| Ry | Psittacosis | ND | | 0(512)*** | | 1 | — |
| $V_2$-1220 | Psittacosis | ND | | 0(256) | | 1 | — |
| 571 | Chancroid | ND | 0 | 0 | | | |
| 564 | Chancroid | ND | 0 | 0 | | | |
| | Normal**** | — | 0 | 0 | | | |

*Abbreviations: ND, not done; Bu, bubo; Ur, urethra; Cx, cervix; Ey, eye.
**Reciprocal of serium dilution in the micro-innunofluorescence antibody test; 0., no antibody.
***( ), Complement fixation titers against psittacosis antigen.
****A total of 10 normal sera were tested.

Controls: Monospecific antisera to antigen-0.65 did not react with any of the reasonable control antigens: group antigen of *C. trachomatis* has been purified. On the other hand, micro-IF with whole organisms has been used for both serodiagnosis of infections and classification of chlamydial strains.

The present invention utilizes a different approach. It was sought directly to detect major antigens toward which humans make antibody by using a sensitive analytical serologic technique: two-dimensional immunoelectrophoresis. This approach was chosen because it is extraordinarily difficult and expensive to prepare large quantities of chlamydiae for classical antigenic analysis and the organisms are complex antigenically. In terms of a serologic test for chlamydial infections, the ideal antigen would be one which was species-specific and toward which humans usually made antibody during the course of infection and disease. One such antigen which has an electrophoretic mobility of 0.65 relative to bovine albumin has been determined and identified. This antigen was common to Trachoma and LGV strains. Most important, all of the humans tested (with LGV, OT, and NGU and from whom *C. trachomatis* has been isolated) showed strong precipitins to antigen-0.65. The most intense precipitins were produced by patients with systmeic infection, whereas those with the more local infections produced a lesser but still definite response.

It was possible to define clearly the presence of antigen-0.65 in chlamydiae. First, the electrophoretic mobility of the antigen was 0.65 ($\pm$ 1.4%) in all strains tested in contrast to the electrophoretic heterogeneity of some common antigens in mycoplasmic species, see Thirkill, C. E. and Kenny, G. E., Infect. Immun., 10: 624, 1974 and Thirkill, C. E. and Kenny, G. E., J. Immunol., 114: 1107, 1975. Secondly, it was possible to prepare monospecific antiserum to this component. Crowle et al, see Crowle, A. J., Revis, G. J., and Jarrett, K., Immunol. Commun., 1: 325, 1972, had indicated that two-dimensional immunoelectrophoresis could be utilized as a preparative technique to provide purified immunogens and thus greatly speed the production of monospecific antiserum to given components. Antiserum was prepared by immunizing animals with excised precipitin lines. The resultant monospecific antiserum permitted identification of precipitin peaks produced by human sera as being antigen-0.65 using the suppression technique. Furthermore, it was possible to identify antigen-0.65 in a variety of *C. trachomatis* strains by immunofluorescence with this monospecific serum.

Although the mouse pneumonitis strain is classified as *C. trachomatis* on the basis of morphology and the presence of glycogen in its inclusion, it did not contain antigen-0.65 when tested by two-dimensional immunoelectrophoresis. The cross-reaction demonstrated by immunofluorescence was small: immunofluorescence was weak even at a large antiserum concentration. Furthermore, little cross-reactivity was seen by either double immunodiffusion or two-dimensional immunoelectrophoresis. Thus, on an antigenic basis, this organism appears quite dissimilar to other members of *C. trachomatis*. DNA reassociation studies have suggested that MoPn is phylogenetically positioned between *C. trachomatis* and *C. psittaci* species with DNA homology of about 60% and 10%, respectively, in contrast to the close relationship between Trachoma and LGV strains.

Two-dimensional immunoelectrophoresis proved to be a powerful analytical tool for detection of antigens important to human infections. The fact that it can be used as a preparative technique for preparation of monospecific antiserum is very useful, because it is a direct approach to antigenic analysis which bypasses the more difficult biomechanical methods. However, this technique for serodiagnosis of human infections is not preferred because this technique is insensitive for measurements of antibody and large amounts of serum are required.

As indicated hereinabove, the subject antigen after purification by immunoadsorption chromatography, was found to be useful for the detection of the antibody to this antigen by counterimmunoelectrophoresis in the diagnosis of *C. trachomatis* infections. The antibody was found in 43 of 45 (96%) of sera from patients with LGV, although no positive reactions were observed in 50 patients with NGV, even though these patients had evidence of antibody as measured by microimmunofluorescence with whole organism antigen. No positive reactions were found in the sera of normal individuals, persons with gonorrhea or in two patients with psittacosis. It is seen from the above, therefore, that counterimmunoelectrophoresis using the purified *C. trachomatis* protein antigen of this invention appears to be a specific serological test for the diagnosis of LGV.

The following is a description of the experiments carried out employing the specific antigen of this invention involving human sera obtained from patients with LGV, NGU, gonorrhea (GC), psittacosis and normal persons.

LGV sera: Fifty-four LGV sera were tested. All sera had antibodies against LGV by either complement fixation (CF), radioisotope precipitation or micro-immunofluorescence (micro-IF) tests and 3 cases were isolation positive. Eighteen cases had antibodies against LGV by micro-IF and LGV organisms were isolated by HeLa 229 cell culture in 4 cases. The remaining 9 cases had no demonstrable antibody by micro-IF and were also isolation negative.

Nongonococcal urethritis (NGU) sera: Fifty NGU patients' sera were tested. Thirty-eight of the NGU patients' sera had detectable antibodies to *C. trachomatis* by micro-IF.

Gonorrhea sera: Ten gonorrhea patients' sera were tested. All were isolation positive for gonococcus but negative for *C. trachomatis* by both isolation and micro-IF testing.

Psittacosis sera: Only 2 psittacosis sera were tested. The sera had CF antibody titers against psittacosis of 1:256 and 1:512 but had no micro-IF antibody against *C. trachomatis* organisms.

Normal control sera: Fifty normal control sera were tested. None had detectable micro-IF antibody for *C. trachomatis*.

Serological test antigen

A purified *C. trachomatis* protein antigen was used as serological test antigen. This component is referred to as antigen-0.65. The antigen was solubilized from LGV-434 organisms using the non-ionic detergent Triton-X-100 and purified by immunoadsorption chromatography. The protein concentration of the antigen used in counterimmunoelectrophoresis was 30 $\mu$g/ml. A very small amount of purified antigen is required for counterimmunoelectrophoresis. For example, 2 microliters of antigen at 30 $\mu$g/ml (60 $\gamma$g) was successfully used. One milliliter of antigen at 30 $\mu$g/ml provides enough antigen to test 500 sera.

Counterimmunoelectrophoresis

A counterimmunoelectrophoresis method described by Kenny et al, Correlation of circulating capsular polysaccharide with bacteremia in pneumococcal pneumonia. Inf. Immun., 6:431-437, for the detection of pneumococcal polysaccharide was used. Briefly, 3 ml of 0.5 agarose containing 0.5% Triton-X-100 in 0.05 ionic strength barbital buffer, pH 8.6 was added to agarose precoated glass slides (25 × 75 mm). The agarose was spread evenly over the slides and allowed to solidify. Eight wells (2 rows of 4) two mm in diameter were cut in the agarose. Two microliters of antigen (60 ηg) and patients sera were added to respective wells using a microsyringe. Electrophoresis was carried out for 45 minutes at 3 volts/cm with 0.1 ionic strength barbital buffer, pH 8.6 in the baths. Slides were observed immediately after electrophoresis. Slides were rinsed in 10 mM TES [N-tris (hydroxymethyl) methyl-2 aminoethanesulfonic acid] saline (0.15 M NaCl), pH 7.0 and distilled water for 24 hours each, air dried and stained with Coomassie Brilliant Blue. Results were recorded before and after staining. Block titrations were done with selected LGV patients: sera using serial two-fold dilutions of serum and antigen to determine optimum concentrations for precipitation.

A single precipitin line was observed when sera from LGV patients were tested against C. trachomatis protein antigen. The position of the precipitin line was related to the titer of the antiserum as measured by micro-IF: the precipitin line was located closer to the antibody well when sera of low antibody titer were used. Block titrations were done to determine the optimal antibody and antigen concentration for precipitation. Serial two-fold dilutions of LGV patients' sera with micro-IF titers of 1:512, 1:2048 and 1:4096 were tested against serial two-fold dilutions of antigen ranging in concentration from 60 to 1.7 ηg. Optimum conditions for precipitation were found when antigen was used at 30 μg/ml (60 ηg antigen) and serum was used undiluted. Sera from LGV patients with titers of 1:2048 and 1:4096 could be diluted 1:8 and still remain positive. A 1:16 dilution of these sera was negative. Serum from the patients with a titer of 1:512 was positive only when used undiluted. The sensitivity of the test for detecting antibody was not increased by reducing the antigen concentration since dilutions of patients' serum that failed to give positive results with 60 ηg of antigen remained negative when retested against antigen concentrations as low as 1.7 ηg. Increasing the time of electrophoresis or staining the slides did not change the results.

Counterimmunoelectrophoresis with purified protein antigen proved to be a specific and sensitive test for diagnosis of LGV, see Table III herein. Ninety-six percent (41/43) of LGV patients who were either isolation positive or had demonstrable antibody by micro-IF were positive. The two sera that were negative had micro-IF titers of 1:256 and 1:64. In comparison, the positive sera had micro-IF titers of 1:512 or above. Sera from nine patients with clinical LGV but without detectable antibody by micro-IF were negative when tested by counterimmunoelectrophoresis. Counterimmunoelectrophoresis was not found useful in detecting antibody in patients with NGU: none of the 50 sera tested was positive. The highest micro-IF titer in the NGU sera studied was 1:256. To evaluate the possibility that the negative results were due to antigen excess, selected NGU patients' sera retested using serial twofold dilutions of antigen varying 30 to 1.7 ηg. Varying the antigen concentration did not change the results. Sera from controls, patients with psittacosis or gonorrhea were negative when tested by counterimmunoelectrophoresis.

TABLE III

Prevalence of Antibody to C. trachomatis Specific Antigen in Human Sera from patients with Lumphogranuloma Venereum and Control Individuals as Determined by Counterimmunoelectrophoresis

| Disease | Number of sera tested | Mean Micro-IF titer[a] | Number of sera positive by counterimmuno-electrophoresis | Percent positive |
|---|---|---|---|---|
| Lymphogranuloma venereum | | | | |
| Antibody[b] and isolation positive | 13 | 2,186 | 12 | |
| Antibody[b] positive, isolation negative | 32 | 2,778 | 31 | |
| Group Total | 45 | 2,607 | 43 | 96% |
| Lymphogranuloma venereum-like | | | | |
| Antibody[b] and isolation negative | 9 | Negative | 0 | 0 |
| Nongonococcal urethritis[c] | 50 | 39 | 0 | 0 |
| Gonorrhea | 10 | Negative | 0 | 0 |
| Psittacosis | 2 | Negative | 0 | 0 |
| Normal | 50 | Negative | 0 | 0 |

[a]Indirect microimmunofluorescent antibody test; titers expressed as reciprocal of serum dilution.
[b]As determined by Micro-IF
[c]38 of 50 sera had demonstrable C. trachomatis antibody as determined by Micro-IF False positive tests were not found from human control sera, gonorrhea or psittacosis patients' sera. An interesting finding was that 9 patients who were clinically diagnosed as having LGV were isolation negative and antibody specific for C. trachomatis was not detected by either micro-IF or counterimmunoelectrophoresis from these patients' sera.

Counterimmunoelectrophoresis using C. trachomatis protein antigen was not found useful for the detection of antibody from patients with NGU of C. trachomatis etiology. Micro-IF titers of sera from NGU patients are generally low, see Wang, S. P. and Grayston, J. T. 1974. Human serology in Chlamydia trachamatis infection with microimmunofluorescence. J. Inf. Dis., 130:388-397; the mean titer was 1:39 in this study. Such low levels of antibody would not be expected to be detected using counterimmunoelectrophoresis. It had been shown that precipitins to C. trachomatis protein antigen could be identified from sera of NGU, nongonococcal cervicitis and ocular trachoma patients using two-dimensional immunoelectrophoresis. The same sera were negative when tested by counterimmunoelectrophoresis. The difference in results reflects the sensitivity of the methods for the detection of antibody. Two-dimensional immunoelectrophoresis is probably more sensitive for the detection of low levels of antibody since large quantities of serum are used and antigen is electrophoresed against a constant antibody concentration over a very large area. This comparative lack of sensitivity was advantageous for the diagnosis of LGV since sera from most patients had very high micro-IF titers (mean 1:2067 in this study). Clearly, the sensitivity of the test could be increased by using larger serum volumes in the test or by use of isotopically labelled antigen in a radioimmunoassay; this would be advantageous for diagnosis of non-gonococcal urethritis but would be less useful for diagnosis of LGV. The procedure for counterimmunoelectrophoresis is simple and results can be rapidly obtained.

In the foregoing tests purified antigen was employed. In the preparation of the purified *Chlamydia trachomatis* specific antigen of this invention, monospecific antiserum to a species-specific antigen of *Chlamydia trachomatis* (antigen 0.65) was prepared in rabbit using a precipitate from two-dimensional immunoelectrophorograms as immunogen. Fractionated γ-globulins of the monospecific antiserum were coupled to the N-hydroxysuccinimide ester derivatives of agarose which were then used for the immunoadsorbent purification of antigen 0.65 from the non-ionic surfactant or detergent (Triton X-100) solubilized lymphogranuloma venereum ($L_2/434/Bu$) organisms. The isolated antigen was immunochemically pure when tested against rabbit antiserum prepared to LGV-434 organisms using rocket and two-dimensional immunoelectrophoresis. Antigenicity of the antigen was destroyed by protease treatment and heating at 56° C. for 30 minutes for the antigen was stable to ribonuclease, dioxyribonuclease, and at a pH in the range 2.2–10.6. Polyacrylamide gel electrophoresis of the purified antigen showed a major protein band with an apparent molecular weight of 160,000.

The following describes the utilization of immunoadsorbent chromatography for the isolation and purification of antigen-0.65 from Triton X-100 solublized antigens of LGV-434 organisms using the purified γ-globulin fraction of monospecific anti-antigen-0.65 serum immobilized on agarose columns.

Preparation of antigen for immunoadsorbent chromatography. LGV strain $L_2/434/Bu$ was used. The insoluble material from Triton treated organisms was removed by centrifugation at 100,000xg for 1 hour and the supernatant used as antigen for immunoadsorption.

Preparation of monospecific antiserum. Monospecific antiserum (anti-antigen-0.65) against *C. trachomatis* antigen-0.65 was prepared in rabbits. Briefly, precipitin peaks of antigen-0.65 from two-dimensional electrophorograms were excised and resuspended in 1 ml of 0.01 M PBS. The agarose-precipitate material was mixed with an equal volume of Freund's complete adjuvant and injected intradermally in the nuchal and inguinal regions of New Zealand white rabbits. Rabbits were boosted with precipitated antigen alone intramuscularly after 28 days and bled 7–10 days after the final immunization. Each immunization consisted of 12 excised precipitin peaks from electrophorograms per rabbit.

Purification of γ-globulins: The γ-globulin fraction was separated from 80 ml of rabbit anti-antigen-0.65 serum by precipitation at 50% saturation of $(NH_4)_2SO_4$ at 4° C. Precipitated protein was washed twice with 40% $(NH_4)_2SO_4$ and dialyzed first against 0.15 M NaCl followed by 0.01 M phosphate ($PO_4$) buffer, pH 6.5. Batch fractionation using DEAE-sephadex A-50 was used for further purification. Ten grams of DEAE-sephadex was equilibrated sequentially in 0.2 M $PO_4$ buffer at pH 6.5 and 0.01 M $PO_4$ buffer, pH 6.5 for 48 hours each with frequent buffer changes. Excess buffer was removed by aspiration using Whatman #5 filter paper and a Buchner funnel. The moist cake was added to 20 ml of the γ-globulin (partially purified by $(NH_4)_2SO_4$ precipitation). The slurry was kept at 4° C. for 1 hour and the unadsorbed γ-globulin removed by aspiration and saved. The cake was washed once with 25 ml of 0.01 M $PO_4$ buffer and the washing pooled with the original eluate. Gamma-globulins were reprecipitated at 50% saturation of $(NH_4)_2SO_4$ and the precipitate resuspended in 20 ml of 0.15 M NaCl. The solution was then dialyzed against 0.15 M NaCl followed by 0.1 M $PO_4$ buffer, pH 7.0 for 72 and 24 hours, respectively. The protein concentration of purified γ-globulin was determined by the method of Lowry, see Lowry, O. H., Rosenbrough, N. J., Farr, A. L. and Randall, R. J. 1951. Protein measurement and the folin phenol reagent. *J. Biol. Chem.*, 193–265–275. Purity of isolated γ-globulin was determined by immunoelectrophoresis.

Immunoadsorbent chromatography. Affi-Gel 10 (Bio-Rad Laboratories, Richmond, Calif.) was used for immunoadsorbent chromatograph. Affi-Gel 10 is an agarose gel in bead form with added aliphatic arms terminated by active carboxy N-hydroxysuccinimide esters, see Cuatrecasas, P. and Parikh. 1972. Adsorbents for affinity chromatography. Use of N-hydroxysuccinimide esters of agarose. *Biochemistry,* 11:2291–2299. Twenty milliliters of purified anti-antigen-0.65 γ-globulin (120 mg protein) in 0.1 M $PO_4$ buffer, pH 7.0 were added to 2 gm of Affi-Gel 10. Coupling was done at 4° C. for 16 hours with gentle mixing. After coupling was completed, the suspension was thoroughly washed with 0.01 M $PO_4$ buffer containing 1 M NaCl, pH 7.0, until absorbence of washing at $OD_{260}$ was zero. Columns, 4.5 cm long × 3.5 cm in diameter, were packed and then washed with 0.05 M PBS containing 0.5% Triton X-100 and 0.01% sodium azide. Triton solubilized LGV-434 organisms were applied to the column in an amount equal to the void volume of the column (typically 5–7 ml of antigen with a protein concentration of 7–10 mg/ml). The column containing antigen was incubated for 1 hour at room temperature. Unadsorbed antigens were removed by washing the column with 50 ml of buffer containing 0.5% Triton followed by an additional 50 ml of 0.05 M PBS containing 0.1% Triton. Adsorbed antigen was eluted with 30 ml of 2 M sodium iodide (NaI) in 0.05 M PBS containing 0.1% Triton. Fractions were collected in 2 ml volumes and immediately dialyzed against 0.01 M PBS for 24 hours. Fractions were monitored for antigen-0.65 by rocket immunoelectrophoresis against monospecific antiserum to antigen-0.65. Fractions containing antigen were pooled and concentrated to approximately 2 ml with centriflo membrane cones CF-50 (Amicon Corp., Lexington, Mass.).

Rocket and two-dimensional immunoelectrophoresis: Rocket immunoelectrophoresis was done on glass mounting slides (4 × 4 cm) covered with 3 ml of supporting matrix consisting of 0.5% agarose in pH 8.6 barbital buffer ionic strength 0.05 containing 0.5% Triton X-100. Wells 3 mm in diameter were cut along one edge of the slide. Agar adjacent to the wells was removed and replaced with 1.8 ml of agarose containing antibody. Slides were electrophoresed for 5 hours at 2.7 volts/cm. Areas of immunoprecipitates were determined from rocket immunograms by multiplying the height of a peak by its width (measured at the point that bisected the peak's height). Two-dimensional immunoelectrophoresis was done. Briefly, antigen was electrophoresed in the first dimension at 2.7 volts/cm for 1 hour and 50 minutes. The second dimension gel was 1.8 ml of agarose containing antiserum. Second dimension electrophoresis was carried out at 2.7 volts/cm for 6 hours.

Polyacrylamide gel electrophoresis: Disc gel polyacrylamide electrophoresis in the presence of 0.1% sodium dodecyl sulfate (SDS) was done according to the method of Laemmli, see Laemmli, U. K. 1970. Clevage of structural proteins during the assembly of the head of bacteriophage T4. *Nature* (London), 227:680–685. Samples were mixed with an equal volume of sample buffer so that the final mixture contained 0.0625 M Tris-hydrochloride (pH 6.8), 2% SDS, 5% mercaptoethanol, 10% glycerol and 0.001% bromophenol blue. The stacking gel contained 3%, the separating gel 8% acrylamide. Samples were boiled for 2 minutes and electrophoresed on a gel column of 9 cm length and 6 mm diameter at 2.5 ma/gel for 3.5 hours. Gels were stained in 0.2% Coomassie Brilliant Blue and destained in a 10% methanol and 7% acetic acid solution at 30° C. B-galactosidase (MW 130,000), catalase (MW 58,000) and myoglobulin (MW 17,200) were used as standard protein markers. Approximate molecular weights of purified antigen were estimated by co-migration of markers in parallel gels.

Characterization of purified antigen: Fifty microliters of purified antigen-0.65 were evaporated under $N_2$ in 450 $\mu$l plastic microfuge tubes. Antigen was resuspended in 50 $\mu$l of the following solutions: Pronase (100 $\mu$g/ml), trypsin (100 $\mu$g/ml), deoxyribonuclease (DNase) (100 $\mu$g/ml), ribonuclease (RNase) (100 $\mu$g/ml), 0.1 M glycine-HCl buffered at pH 2.2, 0.1 M glycine-NaOH buffered at pH 10.6 and 0.05 M sodium metaperiodate. The sources and specifications of the enzymes used are as follows: pronase, B grade (CalBiochem, San Diego, Calif.); trypsin, B grade (CalBiochem); deoxyribonuclease 1, (Sigma, St. Louis, Mo.); and ribonuclease 5X crystallized A grade (CalBiochem). Enzyme solutions were prepared in 0.01 M PBS, pH 7.0 and periodate in 0.05 M sodium acetate buffer pH 4.5. Trypsin, pronase, DNase and RNase were incubated with antigen at 37° C. for 2 hours. Treatment with glycine-HCl, glycine-NaOH and periodate was carried out at 4° C. for 24 hours. Heat treatments of antigen were done at 56°, 80° and 100° C. for 30 minutes. Controls consisted of evaporated antigen resuspended in buffer alone and incubated at 37° C. for 2 hours or 4° C. for 24 hours. The effect of treatment on the antigenicity of antigen-0.65 was determined by two-dimensional immunoelectrophoresis using monospecific antiserum in the second phase of electrophoresis.

Removal of excess detergent from purified antigen-0.65: Initial attempts to determine the protein concentration of purified antigen 0.65 by the Lowry method were unsuccessful due to the presence of excess Triton. Since the protein concentration of the purified antigen was small, it was not possible to dilute away from Triton as had been done when quantitating protein from Triton solubilized LGV-434 organisms. It has been recently shown that ethanol-ethylene glycol disassociates micelles of Triton into monomers that can be removed by ultrafiltration, see Frasch, C. E. 1975. Removal of detergent by ultrafiltration. Dialog published by Amicon Corp., Lexington, Mass., Vol. 7, No. 2.

Purified antigen was mixed with three volumes of ethanol-ethylene glycol in 0.01 M PBS so that the final concentration of ethanol and ethylene glycol was 10 and 30 percent, respectively. The mixture was concentrated 5 times using Centriflo CF-50 cones, washed and concentrated three times in PBS and finally resuspended in 2 ml of 0.01 M PBS.

Purification of antigen-0.65 by immunoadsorbent chromatography: The purity of fractionated $\gamma$-globulins from monospecific rabbit serum was tested by immunoelectrophoresis against goat antibody to rabbit serum. A single precipitin line with $\gamma$-globulin electrophoretic mobility was observed. Coupling to Affi-Gel 10 was efficient: in a typical experiment 80% or greater of the total $\gamma$-globulin fraction from monospecific serum was coupled as determined by protein analysis of the supernatant.

The recovery of antigen 0.65 after elution with NaI was monitored by rocket immunoelectrophoresis. This material appeared immunochemically pure since a single precipitin peak was present above the well containing the concentrated fractions after NaI elution when electrophoresed into anti-LGV-434 serum. In contrast, numerous components were observed with Triton solubilized LGV-434 antigen both before affinity chromatography and in the void volume after immunoadsorption. The immunochemical purity and identification of the purified component as antigen 0.65 was further demonstrated by coelectrophoresis of the Triton X-100 solubilized antigens of LGV-434 organisms with the purified antigen. Peak 0.65 is clearly shown to be enhanced after coelectrophoresis with purified antigen-0.65. No other precipitin peaks were enhanced.

No effect on antigenicity was observed after ethanol-ethylene glycol treatment. Treated antigen remained soluble and the detergent concentration was reduced so that protein concentration could be determined.

Polyacrylamide gel electrophoresis: Disc gel electrophoresis of purified antigen-0.65 resulted in a major staining band. The protein was calculated to have an apparent molecular weight of 160,000. Three minor protein bands were also detectable when 6 $\mu$g of purified antigen (approximately one-tenth of the total preparation) was electrophoresed. The minor protein bands were not observed when gels were loaded with 2 $\mu$g of purified antigen, whereas the major band was distinctly stained. Absorbence scans at 600 $\mu$M of Coomassie Brilliant Blue stained gels showed that 95 percent of the stain was associated with the slower migrating protein band, indicating that the 160,000 M.W. protein was the major component in the purified preparation. Polyacrylamide gel electrophoresis of three different preparations gave the same results for purity and molecular weight.

Partial characterization of purified antigen-0.65: The results of various treatments on purified antigen-0.65 were determined by two-dimensional immunoelectrophoresis of the treated preparations. Antigen was analyzed immediately after treatment since the small volumes of reaction mixtures prevented the removal of various enzymes from the solution. Two $\mu$g of bovine serum albumin (BSA) was added to wells containing treated antigen prior to electrophoresis. BSA served as a marker and an internal control for possible effects of proteolytic enzymes on the antibody during the second phase of electrophoresis. Antigenic activity was destroyed by pronase, trypsin and heating at 56° C. for 30 minutes, whereas it was not affected by DNase, RNase, pH 2.2 or pH 10.6 treatment. However, antigen was altered following evaporation under $N_2$ or incubation at 37° C. for 2 hours; because a more electronegative component appeared. The more anodal antigen reacted with a reaction of identity with the major 0.65 peak indicating a common antigenic determinant. Similar profiles were observed with each of the various treatments in which antigenicity was not destroyed with the exception of periodate oxidation. A single precipitin peak was found after periodate treatment and the electrophoretic mobility of the antigen was changed from 0.65 to 1.2.

A species-specific antigen was purified from *Chlamydia trachomatis* which appears to be a protein of approximately 160,000 molecular weight. The antigen is fairly labile in that antigenic activity was destroyed at 56° C. and altered by both drying and exposure to 37° C. for several hours; however, it was stable over extremes of pH of 2.2 and 10.6. Fortunately, although antigen-0.65 was somewhat labile, its stability was sufficient to permit recovery from immunoadsorbent columns. Thus, complicated chemical fractionation procedures with the attendant losses at each step were avoided and the entire study was greatly expedited. Accordingly, fractionation of antigen-0.65 was accomplished in a single step with an increase in specific antigenic activity of 90-fold over the original Triton treated antigen.

The antigen was shown to be of high purity both immunochemically and by polyacrylamide gel electrophoresis, though the amount of material presently available for characterization is small (approximately 120 μg per liter of infected L cell culture). The yields of recovered antigen are respectable since purification was extremely rapid and the amount of material which can be purified is only limited by the amount of organisms which can be grown.

The *C. trachomatis* specificity of antigen-0.65 and its possible significance serodiagnostically for the diagnosis of *C. trachomatis* infections has been demonstrated herein. Since the antigen's general biochemical nature has been determined, it is also referred to herein as *C. trachomatis* protein antigen (CTP antigen), as well as antigen-0.65.

In the recovery and/or preparation of the solubilized antigen in accordance with the practices of this invention an non-ionic surfactant, such as Triton X-100, was employed. Other suitable non-ionic surfactants are useful. The employed Triton surfactant, Triton being a trademark of Rohm & Haas Company for surfactants based on alkylaryl polyether alcohols, sulfonates and sulfates of non-ionic types was found to be suitable.

Antigen-containing compositions in accordance with this invention might be stored for an extended period of time, such as for months, when maintained at a low temperature, e.g. below freezing, and in a suitable carrier or environment, such as in an aqueous solution or dispersion maintained at a pH in the range 7–8.6 in the presence of a low salt content, e.g. sodium chloride, or in the presence of a suitable buffer, e.g. barbital buffer. Antigen-containing compositions in accordance with this invention may also be lyophilized and stored. If desired, the antigen could be deposited within wells provided in an agarose coating on a glass slide in the form suitable for the electrophoretic determination of LGV antibody in the serum of a patient suspected of LGV.

It has been indicated hereinabove that the antigen of this invention may be isotopically labeled, such as labeled with a radioactive element or group. Such a radioactive isotopically labeled antigen would be especially useful in a radioimmunoassay test for the diagnosis of NGU. Other means or techniques for the labeling of the antigen of this invention, such as enzyme labeling, fluorescent labeling, chemical labeling, to improve the efficacy of the antigen in serological diagnosis would be useful.

As will be apparent to those skilled in the art in the light of the foregoing disclosure, many modifications, alterations and substitutions are possible in the practice of this invention without departing from the spirit or scope thereof.

We claim:

1. *Chlamydia trachomatis* specific antigen useful for the serological diagnosis of lymphogranuloma venereum, said antigen having a molecular weight of about 160,000, being stable to ribonuclease and deoxyribonuclease and at a pH in the range 2.2–10.6 but whose antigenicity is destroyed by protease treatment and heating at a temperature of 56° C. for about 30 minutes.

2. Radioactive isotopically labeled *Chlamydia trachomatis* specific antigen of claim 1.

3. An aqueous composition comprising the antigen of claim 1, said composition having a pH in the range from about 7 to about 8.6 suitable for low temperature storage.

4. An aqueous composition comprising the antigen of claim 2, said composition having a pH in the range from about 7 to about 8.6 suitable for low temperature storage.

5. A method of preparing *Chlamydia trachomatis* antigen which is consistently precipitated by sera of patients with *C. trachomatis* infections which comprises solubilizing *C. trachomatis* in the presence of a non-ionic surfactant and recovering the resulting solubilized *C. trachomatis* antigen by immunoadsorption chromatography employing monospecific antiserum to said antigen as a specific ligand for said antigen.

6. A method in accordance with claim 5 wherein said non-ionic surfactant is a 1% (volume/volume) solution of an alkyl aryl polyether alcohol.

7. A method of isolating *Chlamydia trachomatis* antigen in the form of its antigen-antibody complex which comprises solubilizing *C. trachomatis* antigen and subjecting the resulting solubilized antigen to two-dimensional immunoelectrophoresis and recovering the antigen-antibody complex.

8. A method in accordance with claim 7 wherein said *C. trachomatis* antigen is solubilized by means of an non-ionic surfactant.

9. A method of preparing monospecific antiserum to antigen of *Chamydia trachomatis* which comprises solubilizing the antigens of *C. trachomatis* in the presence of a non-ionic surfactant, subjecting the resulting solubilized antigens to two-dimensional immunoelectrophoresis on agarose, thereby precipitating the *C. trachomatis* antigen as an antigen-antibody complex, recovering said antigen-antibody complex, introducing said resulting recovered antigen-antibody complex into rabbit, thereby causing the production of antiserum therein and recovering rabbit serum containing the resulting produced antiserum.

10. A method for the serological testing of antibody of *Chlamydia trachomatis* which comprises subjecting serum of suspected lymphogranuloma venereum patients to counterimmunoelectrophoresis on agarose employing the antigen of claim 1 in said counterimmunoelectrophoresis, observing during said counter immunoelectrophoresis for the presence of resulting antigen-antibody complex, and detecting said complex by staining said agarose containing said antigen-antibody complex with a suitable dye.

11. A method for the serological testing of antibody to *Chlamydia trachomatis* which comprises subjecting serum of suspected non-gonococcal urethritis patients to radioimmune assay employing the radioactive isotopically labeled antigen of claim 2 in order to detect formation of antigen-antibody complex.

12. A lyophilized composition containing the antigen of claim 1.

13. A lyophilized composition containing a radioactive isotopically labeled antigen of claim 2.

14. A stable composition containing the antigen of claim 1 at a concentration of about 30 $\mu$g/ml.

15. An agarose coated inert substrate, the agarose coating on said substrate being provided with at least two wells cut thereinto, one of said wells having deposited therein the antigen of claim 1 and another of said wells being suitable for the placement therein of serum from a patient for the diagnosis of lymphogranuloma venereum.

16. An agarose coated inert substrate in accordance with claim 15 wherein said well has antigen deposited therein in an amount of about 60 $\eta$g.

17. An agarose coated substrate in accordance with claim 15 wherein said inert substrate is a glass slide.

18. An agarose coated inert substrate in accordance with claim 15 wherein said agarose coating comprises an non-ionic detergent together with a barbital buffer, said agarose coating having been applied at a pH of about 8.6.

* * * * *

UNITED STATES PATENT AND TRADEMARK OFFICE
CERTIFICATE OF CORRECTION

PATENT NO. : 4,118,469
DATED : October 3, 1978
INVENTOR(S) : Harlan D. Caldwell et al It is certified that error appears in the above-identified patent and that said Letters Patent are hereby corrected as shown below:

Column 6, under Table I, second column under "Giemsa" fifth line, "++" should correctly read -- + --; third column under "Indirect FA*", fifth line, in the blank space there should be inserted -- + --;

Column 7, line 9, "than" should correctly read -- then --;

Column 7, under Table II, fourth column under "Site of Isolation", the last three zeroes should be omitted; seventh column under "No. Precipitin Lines vs LGV-434 Ag", under the last "1", three zeroes should be inserted;

Column 12, line 19, after "sera" insert the word -- were --

Column 16, line 47, "µM" should correctly read -- ηM --;

Signed and Sealed this

Twenty-fourth Day of April 1979

[SEAL]

Attest:

RUTH C. MASON
Attesting Officer

DONALD W. BANNER
Commissioner of Patents and Trademarks